(12) United States Patent
Lewinska et al.

(10) Patent No.: US 12,357,555 B2
(45) Date of Patent: Jul. 15, 2025

(54) SELF-EMULSIFYING COMPOSITION, INTENDED FOR ADMINISTRATION ONTO THE SKIN, CONTAINING BIOSURFACTANT, COSURFACTANT AND OIL PHASE

(71) Applicant: INVENTIONBIO SPOLKA Z OGRANICZONA ODPOWIEDZIALNOSCIA, Bydgoszcz (PL)

(72) Inventors: Agnieska Lewinska, Wroclaw (PL); Urszula Bazylinksa, Wroclaw (PL); Marcin Lukaszewicz, Wroclaw (PL)

(73) Assignee: INVENTIONBIO SPÓKA Z OGRANICZON ODPOWIEDZIALNOCIA, Bydgoszcz (PL)

( * ) Notice: Subject to any disclaimer, the term of this patent is extended or adjusted under 35 U.S.C. 154(b) by 386 days.

(21) Appl. No.: 17/904,664

(22) PCT Filed: Feb. 20, 2020

(86) PCT No.: PCT/IB2020/051416
§ 371 (c)(1),
(2) Date: Aug. 19, 2022

(87) PCT Pub. No.: WO2021/165724
PCT Pub. Date: Aug. 26, 2021

(65) Prior Publication Data
US 2023/0103944 A1 Apr. 6, 2023

(30) Foreign Application Priority Data
Feb. 19, 2020 (PL) .......................... 432956

(51) Int. Cl.
| A61Q 19/00 | (2006.01) |
| A61K 8/06 | (2006.01) |
| A61K 8/39 | (2006.01) |
| A61K 8/41 | (2006.01) |
| A61K 8/42 | (2006.01) |
| A61K 8/64 | (2006.01) |

(52) U.S. Cl.
CPC .................. *A61K 8/64* (2013.01); *A61K 8/06* (2013.01); *A61K 8/39* (2013.01); *A61K 8/42* (2013.01); *A61Q 19/00* (2013.01); *A61K 2800/21* (2013.01); *A61K 2800/596* (2013.01)

(58) Field of Classification Search
CPC ...... A61K 8/64; A61K 8/06; A61K 2800/596; A61Q 19/00
See application file for complete search history.

(56) References Cited

U.S. PATENT DOCUMENTS

| 2011/0257116 A1 | 10/2011 | Kitagawa et al. |
| 2016/0030322 A1 | 2/2016 | Lu et al. |
| 2016/0045424 A1 | 2/2016 | Schwab et al. |
| 2017/0071835 A1 | 3/2017 | Schelges et al. |
| 2017/0071842 A1 | 3/2017 | Schelges et al. |
| 2018/0280261 A1 | 10/2018 | Nioh et al. |

FOREIGN PATENT DOCUMENTS

| CN | 204307112 U | 5/2015 | |
| CN | 105213210 A | 1/2016 | |
| CN | 107049945 A | 8/2017 | |
| CN | 107661287 A | 2/2018 | |
| DE | 202018107327 U1 * | 3/2019 | ............ A61K 33/06 |
| EP | 0820273 B1 | 10/2003 | |
| EP | 3391872 A1 | 10/2018 | |
| JP | 2014073968 A * | 4/2014 | ............... A61K 8/92 |
| KR | 100452165 B1 | 10/2004 | |
| KR | 101440726 B1 | 9/2014 | |
| KR | 101837433 B1 | 3/2018 | |
| WO | WO-2005020950 A1 * | 3/2005 | ............... A61K 8/39 |
| WO | 2006028996 A2 | 3/2006 | |
| WO | 2016141098 A1 | 9/2016 | |

OTHER PUBLICATIONS

English Translation. Leovet. DE-202018107327-U1 (Year: 2019).*
English Translation. Shimizu JP-2014073968-A (Year: 2014).*
Bednarski W, Fiedurek J. (ed.) Podstawy biotechnologii przemyslowej. WNT, Warsaw 2007.
Kosaric N., Biosurfactants in industry. Pure Appl. Chem., 64, 1731 (1992).
Neubert HR. Potentials of new nanocarriers for dermal and transdermal drug delivery. Eur J Pharm Biopharm. 2011;77 1:12.
Campos VEB, Ricci-Junior E, Mansur CRE. Nanoemulsions as delivery systems for lipophilic drugs. J Nanosci Nanotechnol. 2012;12(3): 2881 2890.
Trommer H, Neubert HR. Overcoming the stratum corneum: the modulation of skin penetration: a review. Skin Pharmacol Physiol. 2006; 19(2): 106 121.
Kural FH, Gursoy RN. Formulation and characterization of surfactin-containing self-microemulsifying drug delivery systems (SF-SMEDDS). Hacettepe University Journal of the Faculty of Pharmacy, 2010, 30(2): 171-186.
Wu Y-S, Ngai S-C, Goh B-H, Chan K-G, Lee L-H and Chuah L-H. Anticancer activities of surfactin and potential application of nanotechnology assisted surfactin delivery. Frontiers in Pharmacology; 2017; 8:761. doi: 10.3389/ phar.2017.00761.

(Continued)

Primary Examiner — Michael P Cohen
Assistant Examiner — Toriana N. Vigil
(74) Attorney, Agent, or Firm — Craft Chu PLLC; Andrew W. Chu (57) ABSTRACT

The self-emulsifying composition, intended for administration onto the skin, contains a biosurfactant, a cosurfactant and an oil phase. The weight ratio of the bio surfactant, the cosurfactant and the oil phase is 0.01-96.99% by weight: 0.01-96.99% by weight:3-70% by weight, respectively, where the bio surfactant is surfactin or its salt, and the cosurfactant is 2-(2-ethoxyethoxy)ethanol or cocamidopropyl betaine.

8 Claims, 5 Drawing Sheets

(56) References Cited

OTHER PUBLICATIONS

Joe MM, Bradeeba K, Parthasarathi R, Sivakumaar PK, Chauhan PS, Tipayno S, Benson A, Sa T. Development of surfactin based nanoemulsion formulation from selected cooking oils: Evaluation for antimicrobial activity against selected food associated microorganisms. Journal of The Taiwan Institute of Chemical Engineers 2012; 43: 172-180.

* cited by examiner

SELF-EMULSIFYING COMPOSITION, INTENDED FOR ADMINISTRATION ONTO THE SKIN, CONTAINING BIOSURFACTANT, COSURFACTANT AND OIL PHASE

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The object of the invention is self-emulsifying composition, intended for administration onto the skin, containing biosurfactant, cosurfactant and oil phase.

2. Description of Related Art Including Information Disclosed Under 37 CFR 1.97 and 37 CFR 1.98

Self-emulsifying systems are isotropic systems consisting of a surfactant, a cosurfactant and an oil phase which, when diluted in the appropriate ratio, spontaneously self-emulsify.

Biosurfactants, which are compounds that lower the surface tension, are extracellular metabolites produced by bacteria, yeasts or moulds that may be part of the cell wall (Bednarski W, Fiedurek. (ed.) Podstawy biotechnologii przemyslowej. WNT, Warsaw 2007). These substances are produced by microorganisms, and thanks to their low toxicity, ease of obtaining and interesting properties they can be used in many industries (Kosaric N., Biosurfactants in industry. Pure Appl. Chem., 64, 1731 (1992)). For example, in the cosmetics industry, biosurfactants can be an excellent substitute for synthetic surfactants in the production of shampoos, powders as well as moisturising and protective creams.

Surfactants reduce the tension at the phase boundary, so they can be widely used to create carriers. The characteristic hydrophilic-hydrophobic structure enables encapsulation of compounds showing weak or very weak water solubility, which increases their bioavailability. Improved efficiency and bioavailability is particularly important in systems applied onto the skin. The encapsulation of a hydrophobic substance in a dedicated carrier system facilitates its delivery and penetration into the skin. Lipid nanocarriers, such as liposomes, nanocapsules, lipospheres or other self-organising nanosystems, allow the closure of highly hydrophobic compounds, thus increasing their effectiveness after administration.

The formulations created by this type of surfactant are protected by a patent, e.g. a cosmetic cleansing agent with excellent foaming and cleaning properties, containing bio surfactants, in combination with an anionic surfactant and a thickener (PEG-free cosmetic cleansing agents comprising biosurfactants, US20170071835 A1).

Another application describes cosmetic cleansing agents that include biosurfactants and have prebiotic activity. The prebiotic effect is produced by combining biosurfactants with anionic surfactants. This agent also has excellent foaming and washing properties (Cleansing agents containing biosurfactants and having prebiotic activity US20170071842 A1).

Further inventions relate to e.g. formulations containing certain copolymers and at least one surfactant selected from the group consisting of sulphosuccinates and biosurfactants (Cosmetic formulation containing copolymer and sulfosuccinate and/or biosurfactant, US20160045424 A1).

There are known cosmetics used for skin care, especially in case of its roughness, containing a bio surfactant, particularly MEL-A, MEL-B or MEL-C (Biosurfactant-containing skin care cosmetic and skin roughness-improving agent, US 20110257116 A1).

Also sophorolipids-bio surfactants with glycolipid structure, produced by *Candida bombicola*, can act as a natural moisturiser in creams, shampoos and hair and body gels. One of the inventions relates to a cosmetic and dermatological composition comprising, among others, acid sophorolipid or a sophorolipid associated with a mono- or divalent salt in a concentration of 0.01-30% by weight, and use thereof. The composition may be in the form of a w/o, o/w emulsion, or o/w microemulsion. The sophorolipid-based compositions are useful as anti-free-radical and anti-inflammatory agents (Use of sophorolipids in cosmetic and dermatological compositions, EP 0820273 BI).

Patent WO 2006028996 A2 (Emulsan-alginate microspheres and methods of use thereof), describes emulsion-alginate compositions that may be drug carriers. The compositions of the invention allow avoiding some of the problems related to preparation of microspheres or alginate particles.

Micro- and nanoencapsulation is increasingly used in the market of cosmetics and personal care products. This is due to the fact that most of these types of cosmetic products mostly act on the surface layers of the skin without being able to reach its deeper layers. It is common knowledge that the effectiveness of a cosmetic results directly from the ability of penetration of its active substances through the stratum corneum into the skin. Therefore, enormous progress is being made in developing new carrier systems. The advantages of such structures include, among other things, their ability to protect the active substance from harmful external influences, the possibility of obtaining controlled release of the encapsulated substances, and the possibility of encapsulation of substances which are difficult to dissolve in water. One of the most promising systems that can achieve increased skin penetration are solid lipid particles, liposomes, microemulsions and nanoemulsions (Neubert H R. Potentials of new nanocarriers for dermal and transdermal drug delivery. Eur J Pharm Biopharm. 2011; 77 (I):I 2). Nanoemulsions are widely used in many industries, e.g. in the drug industry, owing to many advantages such as ease of preparation and the possibility of industrial-scale production (Campos V E B, Ricci-Junior E, Mansur C R E. Nanoemulsions as delivery systems for lipophilic drugs. J Nanosci Nanotechnol. 2012; 12 (3): 2881 2890). Nanoemulsions can promote penetration through the skin due to their nanometric size, and their large surface area additionally promotes skin contact (Trommer H, Neubert H R. Overcoming the stratum corneum: the modulation of skin penetration: a review. Skin Pharmacol Physiol. 2006; 19 (2): 106 121).

Application KR100452165 relates to a nanoemulsion comprising phospholipids and a peptide-based surfactant. The phospholipid used is lecithin or lecithin derivative, sterol-1 or sterol derivatives.

Application KR101837433 relates to an oil-in-water (o/w) type nanoemulsion with properties of a low viscosity liquid or paste containing 1 to 10% by weight of inulin lauryl carbamate as a surfactant and 0.01 to 3% sodium surfactin per total weight of the nanoemulsion. Silicone oils, ester oils, hydrocarbon oils, vegetable oils, waxes, sunscreens were used as the oil phase. The oil phase represents 10 to 60% by weight of the nanoemulsion. The nanoemulsion contains 0.001 to 30% by weight of at least one active substance selected from the group comprising water-soluble vitamins.

Application CN107661287 relates to a self-emulsifying saponin supply system characterised in that it contains the following components by weight percent: oil phase (labrafil M 1944CS): 0.05%-0.25%; surfactant (ziyuglycoside): 0.45%-0.65%; surfactant (Tween-20, transcutol P): 0.1%-0.3%.

Application CN107049945 relates to an ivermectin nanoemulsion formulation, which aims to address the problem of low water solubility and poor storage stability of ivermectin. The formulation is characterized in that it contains: ivermectin 0.5-2%, oil phase-ethyl oleate 0.5-5%, polyoxyethylene emulsifier-hydrogenated castor oil (RH-40) 8-30%, emulsifier-transcutol (diethylene glycol monoethyl ether), 1-10% of water.

Application WO2016141098 relates to a non-aqueous topical ophthalmic composition containing oil, a poorly water-soluble drug and one or more surfactants; the composition is capable of self-emulsifying when mixed with an aqueous solution after dripping into the eye; about 5% to about 60% by weight of the composition consists of oil. The composition contains less than 1% by weight of water. The composition also contains one or more co solvents. The nanometric emulsion contains dispersed oil droplets after self-emulsifying in the size range of 10-200 nm.

Application KR101440726 relates to a drug delivery system to the lymphatic system (oral formulation), where the solubiliser is selected from a group comprising transcutol (transcutol HP) (diethylene glycol monoethyl ether), ethanol and propylene glycol.

Application CN204307112U relates to a method for the purification of biosurfactants from fermentation broth, which can be used to produce a cosmetic emulsifier system. The formula describes an apparatus for surfactin separation from the fermentation product.

Application CN105213210 relates to the delivery of a surfactant (surfactin) in the preparation of an anti-aging (or anti-wrinkle) treatment in a cosmetic composition, where the composition contains a surfactant and a pharmaceutically acceptable carrier, excipient, diluents, adjuvant and the like. Preferably, the surfactant is cyclolipidine containing a heptapeptide composed of 7 amino acids (L-aspartic acid, L-leucine, glutamic acid, L-leucine, L-two D-valines, and leucine).

Application US2018280261 (EP3391872) relates to an oil-in-water emulsion composition convenient for external preparations used on the skin, and a method of producing thereof. This invention involves a method of producing an oil-in-water emulsion composition, which includes: a stage of creating an intermediate phase by mixing the first surfactant, the second surfactant and water; a stage of adding the oil phase component to the intermediate phase; and a stage of further addition of the aqueous phase component, in which the first surfactant forms the first phase in at least one aqueous solution at a concentration of 40 to 80 percent by weight, and the second surfactant forms the second phase in at least one aqueous solution at a concentration of 40 to 80 percent by weight. In an embodiment, the first surfactant preferably contains at least one surfactant selected from surfactin and its salts, mannosylerythritol lipids, polyglycerol fatty acid esters, sophorolipids, polyoxyethylene glyceryl fatty acids, fatty acids of polyethylene glycol and phospholipids, preferably polyglycerol ester fatty acid or phospholipid. In this form, the second surfactant preferably contains at least one compound selected from alkyl glycosides having the following formula (1), acyl amino acid lysine and/or their salts, esters of sucrose and fatty acids, alkyl polyglycerol ethers, fatty acid glycosides, and monoalkyl phosphates and their salts, preferably alkyl glycoside or monoalkyl phosphate and its salt.

Application US2016030322A relates to anti-aging treatment consisting of: administration of a cosmetic composition containing surfactin at a concentration between 25-100 mM and pharmaceutically acceptable carriers, excipients, diluents or adjuvants; the anti-aging effect of the cosmetic composition involves the enhancement of sirtuin. Surfactin is a cycloaliphatic peptide containing the heptapeptide (L) Glu-(L) Leu (D) Leu-(L) Val-(L) Asp-(D) Leu-(L) Leu related to beta-hydroxy fatty acid, and the distribution of fatty acids of surfactin is as follows: (1) iso-C13>3 percent; (2) C13>0,65 percent; (3) iso-C14>17 percent; (4) C14<41 percent; and (5) iso-C15<11 percent. The preferred distribution of surfactin fatty acids is as follows: (1) iso-C13>10 percent; (2) C13>25 percent; (3) iso-C14>35 percent; (4) C14<25 percent; and (5) iso-C15<3 percent. A method in which the anti-aging cosmetic composition also contains at least one of the following components: alcohols, esters, complex polysaccharides, peanut oils and vitamins.

The publication Rural F H, Giirsoy R N. Formulation and characterization of surfactin-containing self-microemulsifying drug delivery systems (SF-SMEDDS). Hacettepe University Journal of the Faculty of Pharmacy, 2010, 30 (2): 171-186. refers to self-microemulsifying drug delivery systems (SMEDDS) containing surfactin. According to the authors, the work is the first study describing the implementation of surfactin in a dosage form. The aim of the study was to design and characterise stable SMEDDS formulations containing surfactin as the bioactive compound. At the initial stage of the study, SMEDDS preparations containing various compositions of excipients were prepared using three-component phase diagrams:

Series F1: PEG3000, Gelucire 44/14, Labrasol, Vitamin E
Series F2: PEG3000, Gelucire 44/14, Tyloxapol, Vitamin E
Series F3: PEG3000, Tyloxapol, Labrasol, Vitamin E
Series F4: Propylene glycol, Gelucire 44/14, Labrasol, Vitamin E Then the physical stability of the tested preparations was monitored in order to select the most advantageous proposals. The melting endotherm of surfactin was not observed in the thermogram of the surfactin-SMEDDS formulation, which implies the presence of a strong interaction between surfactin and the excipients in an oil-in-water emulsion.

The results showed that SMEDDS preparations containing vitamin E, Labrasol, Gelucire 44/14 and PEG 3000 in the ratio of 1:1:8:0.5 (% w/w) had the highest physical stability. In the final conclusions, the authors indicate that in the future the bioactivity of surfactin should be investigated in a newly developed SMEDDS (self-microemulsifying drug delivery system) preparation.

The paper Wu Y-S, Ngai S-C, Goh B-H, Chan K-G, Lee L-H and Chuah L-H. Anticancer activities of surfactin and potential application of nanotechnology assisted surfactin delivery. Frontiers in Pharmacology; 2017; 8:761. doi: 10.3389/fphar.2017.00761 indicates that the amphiphilic nature of surfactin allows the formation of nanoparticles such as: polymer nanoparticles, mycelles, microemulsions, liposomes. According to the authors, the use of nanopreparations optimises the delivery of surfactins in anticancer therapy. This publication is a review of the latest literature on anticancer effects of surfactin and potential application of nanotechnology-assisted surfactin delivery. The aim of the study was to analyse and compile the current knowledge about surfactins, their properties, method of biosynthesis, anticancer activity, as well as potential application of nanopreparations for optimal delivery of surfactins.

The authors of the work Joe M M, Bradeeba K, Parthasarathi R, Sivakumaar P K, Chauhan P S, Tipayno S, Benson A, Sa T. Development of surfactin based nanoemulsion formulation from selected cooking oils: Evaluation for antimicrobial activity against selected food associated microorganisms. Journal of The Taiwan Institute of Chemical Engineers 2012; 43:172-180, developed a surfactin-based nanoemulsion using cooking oils such as sunflower, castor, coconut, peanut and sesame oils. The oil phase of the O/W nanoemulsion consists of 14% of selected cooking oils, 3% ethanol and 3% surfactins. The average droplet size of various surfactin-based emulsions is in the range of 72.52 to 875.22 nm, the smallest size being obtained with a sunflower oil formulation. Further studies have shown that surfactin-based sunflower oil nanoemulsion has antibacterial effects against *Salmonella typhi, Listeria monocytogenes* and *Staphylococcus aureus*. It also has a strong antifungal activity against *Rhizopus nigricans, Aspergillus niger* and *Penicillium* sp., and a sporicidal activity against *Bacillus cereus* and *Bacillus circulans*. The obtained results suggest the potential use of surfactin as a food preservative.

BRIEF SUMMARY OF THE INVENTION

The aim of the invention is to create a new self-emulsifying composition for administration onto the skin, containing a biosurfactant.

The essence of the invention is a self-emulsifying composition, intended for administration onto the skin, containing a bio surfactant, a cosurfactant and an oil phase, characterised in that the weight ratio of the biosurfactant, the cosurfactant and the oil phase is 0.01-96.99% by weight: 0.01-96.99% by weight: 3-70% by weight, respectively, where the biosurfactant is surfactin or its salt, and the cosurfactant is 2-(2-ethoxyethoxy)ethanol or cocamidopropyl betaine.

The preferable weight ratio of the biosurfactant, the cosurfactant and the oil phase is 10-50% by weight: 20-50% by weight: 10-50% by weight The preferable weight ratio of the bio surfactant, the cosurfactant and the oil phase is 50% by weight: 30% by weight: 20% by weight Preferably, surfactin is produced by *Bacillus subtilis*.

Preferably, the surfactin salt is sodium surfactin.

Preferably, the oil phase is at least one compound selected from the group comprising: Capmul MCM C8, *Cananga* flower oil, *verbena* oil, tamanu oil, oleic acid, tocopherol in sunflower (*Helianthus annuus*) seed oil, ascorbyl tetraisopalmitate, rapeseed oil, fatty acid esters.

The composition is preferably diluted in water.

The preferable dilution is 10-5000 w/w.

The invention provides the following advantages:
the nanoemulsion produced by mixing the composition according to the invention with water shows good skin penetration capacity; and
the composition according to the invention for administration onto the skin can be used in the cosmetic industry.

BRIEF DESCRIPTION OF THE SEVERAL VIEWS OF THE DRAWINGS

The invention is shown in the figures.

DETAILED DESCRIPTION OF THE INVENTION

The invention is presented in the following non-limiting embodiments. Whereby, the individual components of the composition according to the invention are known and have been tested for toxicity, and the available test results indicate that none of the components exhibit any human toxicity, and each of them can be used to produce a composition applied to human skin.

Embodiment 1

Preparation of self-emulsifying (spontaneous) nanoemulsion formulations co-formed by surfactin (a biosurfactant of bacterial origin, which reduces the interphase tension, so that a nanocarrier can be obtained)

Figure 1:
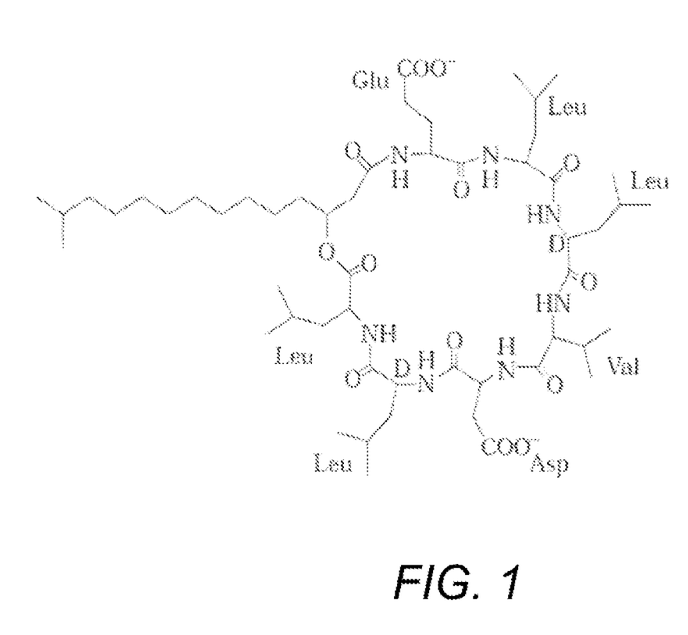
FIG. 1 shows a schematic illustration of the chemical formula of sodium surfactin.

Capmul MCM C8, sodium surfactin (FIG. 1) and 2-(2-ethoxyethoxy)ethanol were thoroughly mixed in a ratio of 40:10:50 w/w to form a concentrate which is the composition according to the invention for administration onto the skin. Then 50 mg of the composition was mixed with 10 ml of water at 37° C. The whole was stirred on a stirrer to obtain an o/w type nanoemulsion with a size of 125.2±1.6 nm, polydispersity index (PdI) of 0.182±0.009, and Zeta potential of −87.86±1.42 mV.

Figure 2:
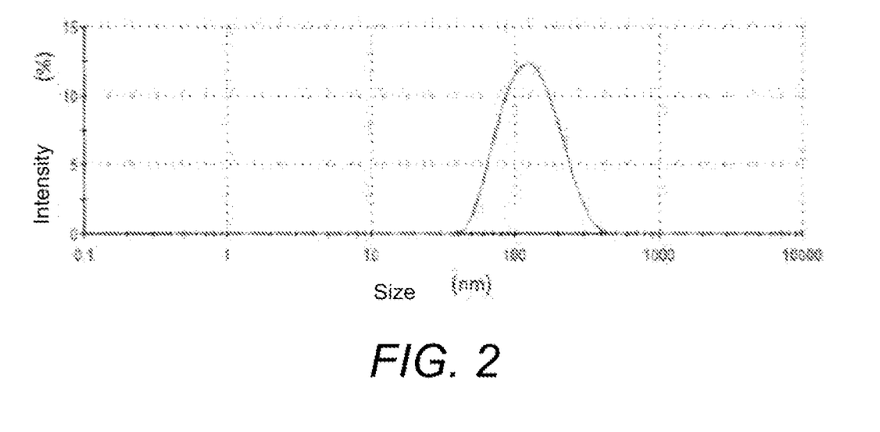
FIG. 2 shows a graph illustration of the size distribution of the nanoemulsion formed after dilution of the concentrate containing Capmul MCM C8, sodium surfactin and 2-(2-ethoxyethoxy)ethanol (40:10:50 w/w) with water in the ratio of 1:100 w/v.
Figure 3:
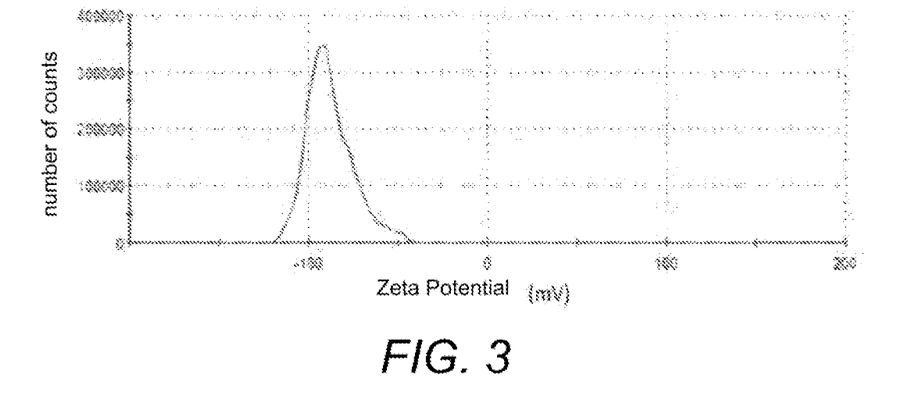
FIG. 3 shows a graph illustration of the distribution of the Zeta potential of the nanoemulsion formed after dilution of the concentrate containing Capmul MCM C8, sodium surfactin and 2-(2-ethoxyethoxy)ethanol (40:10:50 w/w) with water in the ratio of 1:100 w/v.

The concentrate with the composition revealed above, after dilution 1:100 w/v with water, allows to obtain an o/w type nanoemulsion with size of 116.8±0.7 nm, polydispersity index (PdI) of 0.162±0.014 (FIG. 2), and Zeta potential of −87.63±0.98 mV (FIG. 3).

The resulting nanoemulsion can be re-diluted with water to a final dilution of 1:1000 w/v, having the following parameters: size 129.5±0.4 nm, polydispersity index (PdI) 0.153±0.012, Zeta potential −61.2±3.03 mV.

The parameters such as: size (hydrodynamic diameter of nanoemulsion droplets), polydispersity index—PdI, Zeta potential were obtained by means of an appropriate dynamic light scattering (DLS) and electrophoretic light scattering (ELS) techniques.

Embodiment 2

Preparation of self-emulsifying (spontaneous) nanoemulsion formulations co-formed by surfactin, where Capmul MCM C8, sodium surfactin and 2-(2-ethoxyethoxy)ethanol were thoroughly mixed in a ratio of 50:10:40 w/w to form a concentrate which is a composition according to the invention. Then 50 mg of the composition was mixed with 10 ml of water at 37° C. The whole was stirred on a stirrer to obtain an o/w type nanoemulsion with a size of 161.3±4 nm, polydispersity index (PdI) of 0.362±0.021, and Zeta potential of −94,23±4.96 mV.

The concentrate with the composition revealed above, after dilution 1:100 w/v with water, allows to obtain an o/w type nanoemulsion with size of 166.7±4.5 nm, polydispersity index (PdI) of 0.402±0.014, and Zeta potential of −92.6±0.86. The resulting nanoemulsion can be re-diluted with water to a final dilution of 1:1000 w/v, having the following parameters: size 161.7±1.7 nm, polydispersity index (PdI) 0.291±0.023, Zeta potential −63,33±0.66 mV.

Embodiment 3

Figure 4:
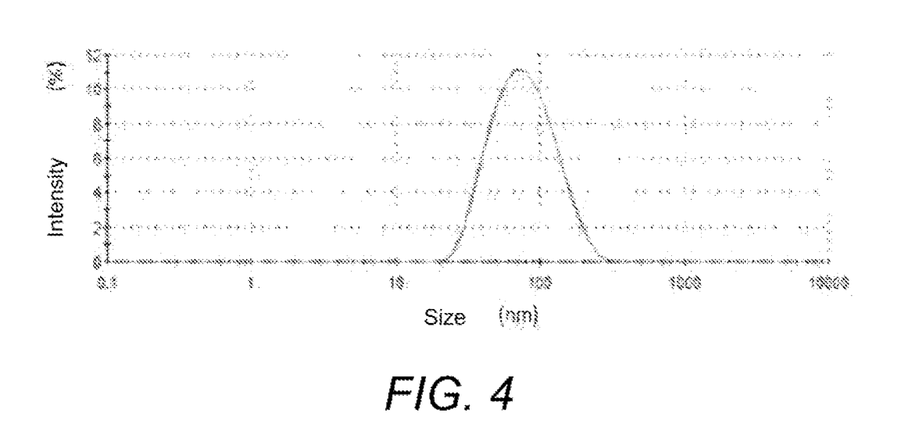
FIG. 4 shows a graph illustration of the size distribution of the nanoemulsion formed after dilution of the concentrate containing Capmul MCM C8, sodium surfactin and 2-(2-ethoxyethoxy)ethanol (50:30:20 w/w) with water in the ratio of 1:100 w/v.

Preparation of self-emulsifying (spontaneous) nanoemulsion formulations co-formed by surfactin, where Capmul MCM C8, sodium surfactin and 2-(2-ethoxyethoxy)ethanol were thoroughly mixed in a ratio of 50:30:20 w/w to form a concentrate which is a composition according to the invention. Then 50 mg of the composition was mixed with 10 ml of water at 37° C. The whole was stirred on a stirrer to obtain an o/w type nanoemulsion with a size of 82.85±0.9 nm, polydispersity index (PdI) of 0.159±0.009 (FIG. 4) and Zeta potential of −90.93±3.09 mV.

The concentrate with the composition revealed above, after dilution 1:100 w/v with water, allows to obtain an o/w type nanoemulsion with size of 67.2±1.2 nm, polydispersity index (PdI) of 0.201±0.005, and Zeta potential of −87.60±1.05 mV. The resulting nanoemulsion can be re-diluted with water to a final dilution of 1:1000 w/v, having the following parameters: size 105.8±0.5 nm, polydispersity index (PdI) 0.071±0.014, Zeta potential −67,93±8.07 mV.

Embodiment 4

Preparation of self-emulsifying (spontaneous) nanoemulsion formulations co-formed by surfactin, where Capmul MCM C8, sodium surfactin and 2-(2-ethoxyethoxy)ethanol were thoroughly mixed in a ratio of 10:50:40 w/w to form a concentrate which is a composition according to the invention. Then 50 mg of the composition was mixed with 10 ml of water at 37° C. The whole was stirred on a stirrer to obtain an o/w type nanoemulsion with a size of 69.6±1.5 nm, polydispersity index (PdI) of 0.287±0.025, and Zeta potential of −87,46±2.20 mV.

The concentrate with the composition revealed above, after dilution 1:100 w/v with water, allows to obtain an o/w type nanoemulsion with size of 59.8±0.9 nm, polydispersity index (PdI) of 0.293±0.037, and Zeta potential of −74.23±0.30 mV. The resulting nanoemulsion can be re-diluted with water to a final dilution of 1:1000 w/v, having the following parameters: size 100.1±0.8 nm, polydispersity index (PdI) 0.139±0.008, Zeta potential −71,86±5.44 mV.

Embodiment 5

Figure 5:
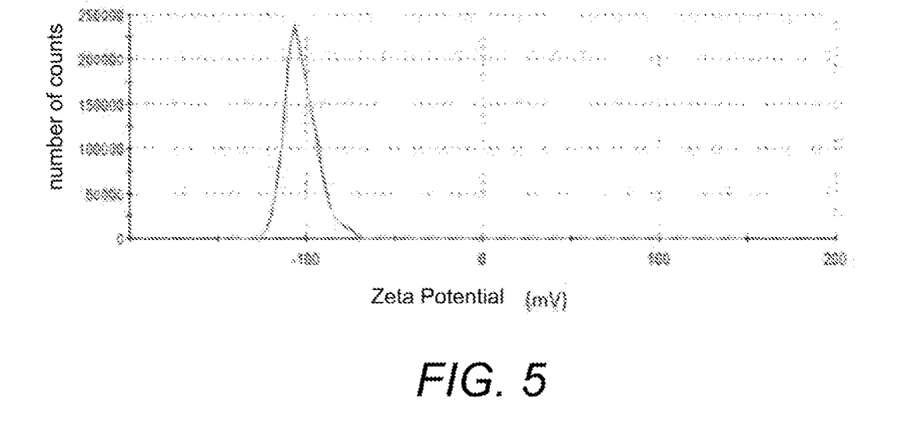
FIG. 5 shows a graph illustration of the distribution of the Zeta potential of the nanoemulsion formed after dilution of the concentrate containing rapeseed oil, sodium surfactin and 2-(2-ethoxyethoxy)ethanol (20:50:30 w/w) with water in the ratio of 1:200 w/v.

Preparation of self-emulsifying (spontaneous) nanoemulsion formulations co-formed by surfactin, where Capmul MCM C8, sodium surfactin and 2-(2-ethoxyethoxy)ethanol were mixed in a ratio of 20:50:30 w/w to form a concentrate which is a composition according to the invention. Then 50 mg of the composition was mixed with 10 ml of water at 37° C. The whole was stirred on a stirrer to obtain an o/w type nanoemulsion with a size of 69.3±1.4 nm, polydispersity index (PdI) of 0.084±0.019, and Zeta potential of −77.36±1.61 mV (FIG. 5).

The concentrate with the composition revealed above, after dilution 1:100 w/v with water, allows to obtain an o/w type nanoemulsion with size of 67.9±0.2 nm, polydispersity index (PdI) of 0.054±0.015, and Zeta potential of −75, 93±2.10 mV. The resulting nanoemulsion can be re-diluted with water to a final dilution of 1:1000 w/v, having the following parameters: size 97.4±0.5 nm, polydispersity index (PdI) 0.027±0.015, Zeta potential −54±6.60 mV.

Embodiment 6

Preparation of self-emulsifying (spontaneous) nanoemulsion formulations co-formed by surfactin, as in embodiment 1, where Capmul MCM C8, sodium surfactin and 2-(2-ethoxyethoxy)ethanol were mixed in a ratio of 3:96.99:0.01 w/w to form a concentrate which is a composition according to the invention. Then 50 mg of the composition was mixed with 5 ml of water at 37° C. The whole was stirred on a stirrer to obtain an o/w type nanoemulsion with a size of 536.63±302.77 nm, polydispersity index (PdI) of 0.684±0.277, and Zeta potential of −99.13±6.16.

Embodiment 7

Preparation of self-emulsifying (spontaneous) nanoemulsion formulations co-formed by surfactin, as in embodiment 1, where Capmul MCM C8, sodium surfactin and 2-(2-ethoxyethoxy)ethanol were thoroughly mixed in a ratio of 3:0.01:96.99 w/w to form a concentrate which is a composition according to the invention. Then 50 mg of the composition was mixed with 5 ml of water at 37° C. The whole was stirred on a stirrer to obtain an o/w type nanoemulsion with a size of 216.86±5.74 nm, polydispersity index (PdI) of 0.439±0.023, and Zeta potential of −69.66±2.85.

Embodiment 8

Preparation of self-emulsifying (spontaneous) nanoemulsion formulations co-formed by surfactin, as in embodiment 1, where Capmul MCM C8, sodium surfactin and 2-(2-ethoxyethoxy)ethanol were mixed in a ratio of 95:2: 3 w/w to form a concentrate which is a composition according to the invention. Then 50 mg of the composition was mixed with 5 ml of water at 37° C. The whole was stirred on a stirrer to obtain an o/w type nanoemulsion with a size of 570.56±7.39 nm, polydispersity index (PdI) of 0.991±0.014, and Zeta potential of −63.06±1.45.

In this embodiment, surfactin produced by *Bacillus subtilis* is used to prepare self-emulsifying emulsions.

Although surfactin produced by *Bacillus subtilis* was used in this non-limiting embodiment, it is possible to use surfactin produced by other species of the *Bacillus* genus, e.g. *B. mojavensis, B. amyloliquefaciens, B. circulans, B. licheniformis.*

Embodiment 9

Preparation of self-emulsifying (spontaneous) nanoemulsion formulations co-formed by surfactin, where *Cananga* oil is used as the oil phase.

*Cananga* oil, sodium surfactin and 2-(2-ethoxyethoxy)ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 174.2±2.3 nm, polydispersity index (PdI) of 0.076±0.010, and Zeta potential of −73.5±1.8 mV.

Embodiment 10

Preparation of self-emulsifying (spontaneous) nanoemulsion formulations co-formed by surfactin, where *Litsea cubeba* oil is used as the oil phase.

The *Litsea cubeba* oil, sodium surfactin and 2-(2-ethoxyethoxy)ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 86.78±4.58 nm, polydispersity index (PdI) of 0.408±0.034, and Zeta potential of −56,83±8.32 mV.

Embodiment 11

Preparation of self-emulsifying (spontaneous) nanoemulsion formulations co-formed by surfactin, where tocopherol is used as the oil phase.

Tocopherol, sodium surfactin and 2-(2-ethoxyethoxy)ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 150.25±52.85 nm, polydispersity index (PdI) of 0.656±0.248, and Zeta potential of −58,83±3.44 mV.

Embodiment 12

Preparation of self-emulsifying (spontaneous) nanoemulsion formulations co-formed by surfactin, where sunflower (*Helianthus annuus*) seed oil is used as the oil phase. Tocopherol represents 70%, and sunflower oil 30%.

Tocopherol in sunflower (*Helianthus annuus*) seed oil as the oil phase, sodium surfactin and 2-(2-ethoxyethoxy) ethanol were carefully mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 183.9±7.64 nm, polydispersity index (PdI) of 0.328±0.01, and Zeta potential of −95,03±5.11 mV.

Embodiment 13

Preparation of self-emulsifying (spontaneous) nanoemulsion formulations co-formed by surfactin, where ascorbyl tetraisopalmitate is used as the oil phase.

Ascorbyl tetraisopalmitate, sodium surfactin and 2-(2-ethoxyethoxy)ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 176.46±0.50 nm, polydispersity index (PdI) of 0.108±0.014, and Zeta potential of −82,7±1.9 mV.

Embodiment 14

Preparation of self-emulsifying (spontaneous) nanoemulsion formulations co-formed by surfactin, where oleic acid is used as the oil phase.

Oleic acid, sodium surfactin and 2-(2-ethoxyethoxy)ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 147.96±2.89 nm, polydispersity index (PdI) of 0.255±0.013, and Zeta potential of −87.63±2.19 mV.

Embodiment 15

Preparation of self-emulsifying (spontaneous) nanoemulsion formulations co-formed by surfactin, where rapeseed oil is used as the oil phase.

Rapeseed oil, sodium surfactin and 2-(2-ethoxyethoxy) ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 780.36±117.67 nm, polydispersity index (PdI) of 0.680±0.033, and Zeta potential of −103.33±1.52 mV.

Embodiment 16

Preparation of self-emulsifying (spontaneous) nanoemulsion formulations co-formed by surfactin, where fatty acid esters are used as the oil phase.

Fatty acid esters, sodium surfactin and 2-(2-ethoxyethoxy)ethanol were thoroughly mixed in a ratio of 20:50:30 w/w to form a concentrate. Then 50 mg of the composition was mixed with 10 ml of water at 37° C. The whole was stirred on a stirrer to obtain an o/w type nanoemulsion with a size of 164.9±2.98 nm, polydispersity index (PdI) of 0.235±0.008, and Zeta potential of −93,46±5.33 mV.

Embodiment 17

Preparation of self-emulsifying (spontaneous) nanoemulsion formulations co-formed by surfactin, where Capmul MCM C8, sodium surfactin and 2-(2-ethoxyethoxy)ethanol were thoroughly mixed in a ratio of 20:50:30 w/w to form a concentrate which is a composition according to the invention. The concentrate contains dissolved curcumin. Then 50 mg of the composition was mixed with 10 ml of water at 37° C. The whole was stirred on a stirrer to obtain an o/w type nanoemulsion with a size of 68.03±0.91 nm, polydispersity index (PdI) of 0.271±0.017, and Zeta potential of −73,40±4.71 mV.

Figure 6:
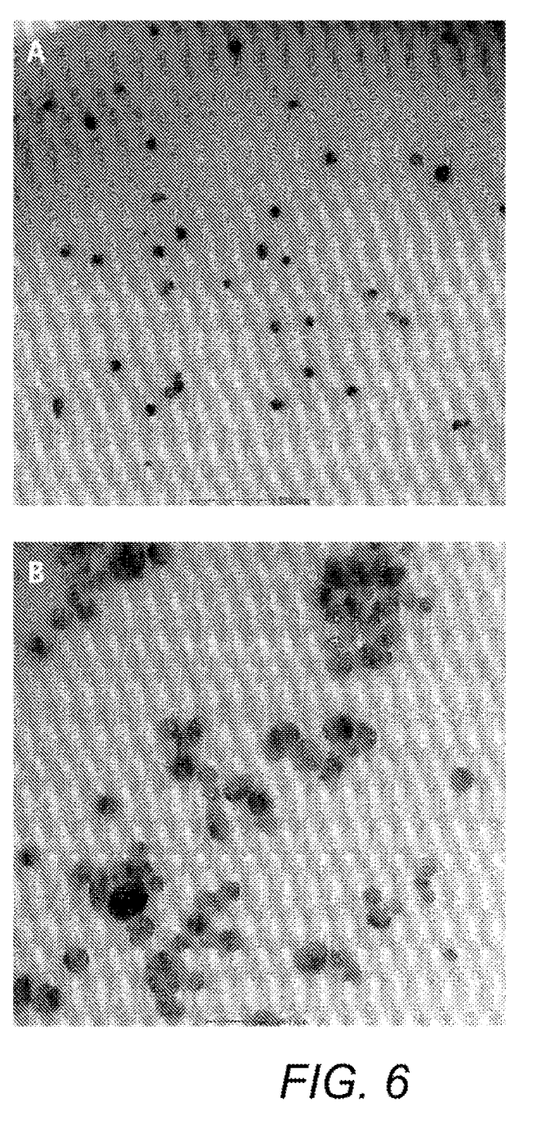
FIG. 6 shows an image of the morphology of the nanoemulsion produced in Embodiment 17 using TEM imaging, where A) is the magnification at 500 nm, B) is the magnification at 200 nm.

Curcumin was chosen as a model bioactive compound used in cosmetics and medicine. The morphology of the obtained emulsion with encapsulated curcumin was presented using transmission electron microscopy (TEM) (FIG. 6). The prepared nanoemulsion was applied on a mesh, after drying it was introduced in a transmission electron microscope and imaged at an accelerating voltage of 80 eV.

Embodiment 18

Preparation of self-emulsifying (spontaneous) nanoemulsion formulations co-formed by surfactin as carriers of active substances.

In this non-limiting embodiment, lidocaine was used as the active substance.

Preparation of self-emulsifying (spontaneous) nanoemulsion formulations co-formed by surfactin, where Capmul MCM C8, sodium surfactin and 2-(2-ethoxyethoxy)ethanol were thoroughly mixed in a ratio of 20:50:30 w/w to form a concentrate which is a composition according to the invention. Then the active substance, lidocaine, was dissolved in the concentrate in the amount of 10 mg in 1 g of oil. Then 50 mg of the composition was mixed with 10 ml of water at 37° C. The whole was stirred on a stirrer to obtain an o/w type nanoemulsion with a size of 60.92±0.11 nm, polydispersity index (PdI) of 0.157±0.021, and Zeta potential of −70,06±4.21 mV.

Embodiment 19

Microscopic analysis of skin penetration by the composition according to the invention was performed.

Figure 7:
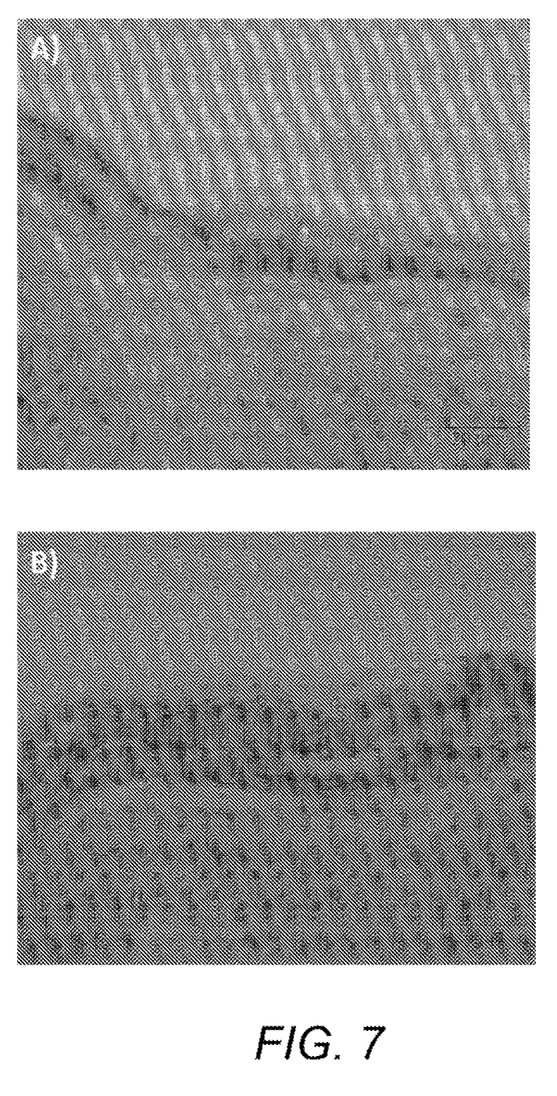
FIG. 7 shows another image of the penetration of a fluorescent dye (coumarin): suspended in the oil phase (A), encapsulated in nanoemulsion according to the invention (B).

A self-emulsifying (spontaneous) nanoemulsion formulation system was prepared, co-formed by sodium surfactin, ascorbyl tetraisopalmitate and 2-(2-ethoxyethoxy)ethanol, thoroughly mixed in a ratio of 20:50:30 w/w to form a concentrate which is a composition according to the invention. Additionally, a fluorescent dye, coumarin, was dissolved in concentrate. Then 50 mg of the composition was mixed with 10 ml of water at 37° C. The whole was stirred on a stirrer to obtain an o/w type nanoemulsion. The control sample was coumarin dissolved in ascorbyl tetraisopalmitate at the same concentration as in the nanoemulsion described above. Samples of the preparations were applied to pig skin prepared from pig ears. The experiment was conducted in Franz chambers for 1 hour. Then tissue imaging was carried out using a confocal microscope, following standard procedures. The results are shown in FIG. 7, which shows good penetration of the nanoemulsion with the fluorescent dye (coumarin) into the skin after 1 hour (FIG. 7B), compared to the control sample (FIG. 7A).

Embodiment 20

Preparation of self-emulsifying (spontaneous) nanoemulsion formulations co-formed by surfactin, where oleic acid, sodium surfactin and cocamidopropyl betaine were thoroughly mixed in a ratio of 10:20:70 w/w to form a concentrate which is a composition according to the invention. Then 50 mg of the composition was mixed with 10 ml of water at 37° C. The whole was stirred on a stirrer to obtain an o/w type nanoemulsion with a size of 143.2±0.5 nm, polydispersity index (PdI) of 0.267±0.025, and Zeta potential of −42.4±5.03 mV.

Embodiment 21

Preparation of self-emulsifying (spontaneous) nanoemulsion formulations co-formed by surfactin, where oleic acid, sodium surfactin and cocamidopropyl betaine were thoroughly mixed in a ratio of 10:20:70 w/w to form a concentrate which is a composition according to the invention. Then 50 mg of the composition was mixed with 30 ml of water at 37° C. The whole was stirred on a stirrer to obtain an o/w type nanoemulsion with a size of 121.32±0.6 nm, polydispersity index (PdI) of 0.198±0.022, and Zeta potential of −74.5±3.03 mV.

Embodiment 22

Preparation of self-emulsifying (spontaneous) nanoemulsion formulations co-formed by surfactin, where oleic acid, sodium surfactin and cocamidopropyl betaine were thoroughly mixed in a ratio of 05:25:70 w/w to form a concentrate which is a composition according to the invention. Then 50 mg of the composition was mixed with 10 ml of water at 37° C. The whole was stirred on a stirrer to obtain an o/w type nanoemulsion with a size of 91.2±0.2 nm, polydispersity index (PdI) of 0.266±0.014, and Zeta potential of −50.4±4.03 mV.

Embodiment 23

Preparation of self-emulsifying (spontaneous) nanoemulsion formulations co-formed by surfactin, where oleic acid, sodium surfactin and cocamidopropyl betaine were thoroughly mixed in a ratio of 05:25:70 w/w to form a concentrate which is a composition according to the invention. Then 50 mg of the composition was mixed with 30 ml of water at 37° C. The whole was stirred on a stirrer to obtain an o/w type nanoemulsion with a size of 80.45±0.6 nm, polydispersity index (PdI) of 0.210±0.021, and Zeta potential of −61.5±2.03 mV.

Embodiment 24

Preparation of self-emulsifying (spontaneous) nanoemulsion formulations co-formed by surfactin, where oleic acid, sodium surfactin and cocamidopropyl betaine were thoroughly mixed in a ratio of 10:30:60 w/w to form a concentrate which is a composition according to the invention. Then 50 mg of the composition was mixed with 20 ml of water at 37° C. The whole was stirred on a stirrer to obtain an o/w type nanoemulsion with a size of 152.41±0.8 nm, polydispersity index (PdI) of 0.216±0.014, and Zeta potential of −52.01±5.16 mV.

Embodiment 25

Preparation of self-emulsifying (spontaneous) nanoemulsion formulations co-formed by surfactin, where oleic acid, sodium surfactin and cocamidopropyl betaine were thoroughly mixed in a ratio of 10:30:60 w/w to form a concentrate which is a composition according to the invention. Then 50 mg of the composition was mixed with 10 ml of water at 37° C. The whole was stirred on a stirrer to obtain an o/w type nanoemulsion with a size of 162.72±0.5 nm, polydispersity index (PdI) of 0.254±0.039, and Zeta potential of −43.01±3.19 mV.

Embodiment 26

Preparation of self-emulsifying (spontaneous) nanoemulsion formulations co-formed by surfactin, where oleic acid, sodium surfactin and cocamidopropyl betaine were thoroughly mixed in a ratio of 10:30:60 w/w to form a concentrate which is a composition according to the invention. Then 50 mg of the composition was mixed with 10 ml of water at 37° C. and the whole was stirred on a magnetic stirrer. Preferably, the obtained nanoemulsion can be diluted 2.5 times with water, resulting in a final dilution of 1:2500 w/v and an o/w type formulation with a size of 65.65±0.4 nm, polydispersity index (PdI) of 0.169±0.053, and Zeta potential of −63.54±2.18 mV.

Embodiment 27

Preparation of self-emulsifying (spontaneous) nanoemulsion formulations co-formed by surfactin, where oleic acid, sodium surfactin and cocamidopropyl betaine were thoroughly mixed in a ratio of 05:25:70 w/w to form a concentrate which is a composition according to the invention. Then 50 mg of the composition was mixed with 10 ml of water at 37° C. Preferably, the obtained nanoemulsion can be diluted 2.5 times with water, resulting in a final dilution of 1:5000 w/v and an o/w type formulation with a size of 68.75±0.3 nm, polydispersity index (PdI) of 0.124±0.036, and Zeta potential of −69.32±1.88 mV.

Embodiment 28

Preparation of self-emulsifying (spontaneous) nanoemulsion formulations co-formed by surfactin, where Capmul MCM C8, sodium surfactin and cocamidopropyl betaine were thoroughly mixed in a ratio of 5:25:70 w/w to form a concentrate which is a composition according to the invention. Then 50 mg of the composition was mixed with 10 ml of water at 37° C. The whole was stirred on a stirrer to obtain an o/w type nanoemulsion with a size of 80.45±0.6 nm, polydispersity index (PdI) of 0.210±0.021, and Zeta potential of −61.5±2.03 mV.

Embodiment 29

Preparation of self-emulsifying (spontaneous) nanoemulsion formulations co-formed by surfactin, where Capmul MCM C8, sodium surfactin and cocamidopropyl betaine were thoroughly mixed in a ratio of 5:25:70 w/w to form a concentrate which is a composition according to the invention. Then 50 mg of the composition was mixed with 20 ml of water at 37° C. The whole was stirred on a stirrer to obtain an o/w type nanoemulsion with a size of 105.83±0.7 nm, polydispersity index (PdI) of 0.289±0.072, and Zeta potential of −53.5±4.02 mV.

Embodiment 30

Preparation of self-emulsifying (spontaneous) nanoemulsion formulations co-formed by surfactin, where Capmul MCM C8, sodium surfactin and cocamidopropyl betaine were thoroughly mixed in a ratio of 5:25:70 w/w to form a concentrate which is a composition according to the invention. Then 50 mg of the composition was mixed with 30 ml of water at 37° C. The whole was stirred on a stirrer to obtain an o/w type nanoemulsion with a size of 110.03±0.7 nm, polydispersity index (PdI) of 0.235±0.024, and Zeta potential of −75.6±2.14 mV.

We claim:

1. A composition, consisting of:
   a bio surfactant at 0.01-96.99% of total weight;
   a cosurfactant at 0.01-96.99% of total weight; and
   an oil phase at 3-70% of total weight so as to be self-emulsifying for administration on skin,
   wherein the biosurfactant is a surfactin or a salt thereof, and
   wherein the cosurfactant is either 2-(2-ethoxyethoxy) ethanol or cocamidopropyl betaine.

2. The composition, according to claim 1, wherein the bio surfactant is at 10-50% of total weight, wherein the cosurfactant is at 20-50% of total weight, and wherein the oil phase is at 10-50% of total weight.

3. The composition, according to claim 1, wherein the bio surfactant is at 50% of total weight, wherein the cosurfactant is at 30% of total weight, and where the oil 2 phase is at 20% of total weight.

4. The composition, according to claim 1, wherein the biosurfactant is a *Bacillus subtilis* surfactin.

5. The composition, according to claim 1, wherein the biosurfactant is a sodium surfactin.

6. The composition, according to claim 1, wherein the oil phase is comprised of at least one compound selected from a group consisting of: glyceryl caprylate, *Cananga* flower oil, *verbena* oil, tamanu oil, oleic acid, tocopherol in sunflower seed oil, ascorbyl tetraisopalmitate, rapeseed oil, and fatty acid esters.

7. A solution consisting of the composition of claim 1 and water.

8. The solution, according to claim 7, wherein the composition is diluted at 10-5000 w/w by the water.

* * * * *